US 6,609,434 B2

(12) United States Patent
Hubbell et al.

(10) Patent No.: US 6,609,434 B2
(45) Date of Patent: Aug. 26, 2003

(54) METHOD OF RETRIEVING A LIQUID SAMPLE, A SUCTION LYSIMETER, A PORTABLE SUCTION LYSIMETER, A LYSIMETER SYSTEM, AND A DEEP LYSIMETER

(75) Inventors: Joel M. Hubbell, Idaho Falls, ID (US); James B. Sisson, Idaho Falls, ID (US)

(73) Assignee: The United States of America as represented by the Department of Energy, Washington, DC (US)

(*) Notice: Subject to any disclaimer, the term of this patent is extended or adjusted under 35 U.S.C. 154(b) by 0 days.

(21) Appl. No.: 10/040,021

(22) Filed: Jan. 3, 2002

(65) Prior Publication Data

US 2003/0121336 A1 Jul. 3, 2003

(51) Int. Cl.[7] .................................................. G01N 1/00
(52) U.S. Cl. .................................. 73/864.51; 73/864.52
(58) Field of Search .......................... 73/863.23, 864.31, 73/864.51, 864.52, 864.62, 864.63, 864.66, 864.67, 864.34, 864.73, 864.74; 166/264

(56) References Cited

U.S. PATENT DOCUMENTS

| | | | | |
|---|---|---|---|---|
| 4,295,801 A | * | 10/1981 | Bennett | 417/397 |
| 4,669,554 A | * | 6/1987 | Cordry | 175/59 |
| 4,692,287 A | | 9/1987 | Timmons | 264/41 |
| 4,759,227 A | | 7/1988 | Timmons | 73/863.23 |
| 4,923,333 A | | 5/1990 | Timmons | 405/128 |
| 5,000,051 A | | 3/1991 | Bredemeier | 73/863.23 |
| 5,035,149 A | * | 7/1991 | Wierenga | 73/863.23 |
| 5,272,910 A | | 12/1993 | Everett et al. | 73/40 |
| 5,465,628 A | | 11/1995 | Timmons | 73/864.34 |
| 5,567,889 A | | 10/1996 | Sullivan et al. | 73/863.23 |
| 5,635,653 A | | 6/1997 | Wittig et al. | 73/864.74 |
| 5,677,499 A | | 10/1997 | Sullivan et al. | 73/863.23 |
| 5,804,743 A | * | 9/1998 | Vroblesky et al. | 73/863.23 |
| 5,864,069 A | | 1/1999 | Sullivan et al. | 73/863.23 |
| 6,318,190 B1 | * | 11/2001 | Radcliffe et al. | 73/863.02 |

* cited by examiner

Primary Examiner—Robert Raevis

(57) ABSTRACT

A method of retrieving a liquid sample comprises providing a portable lysimeter including a semi-permeable membrane and a chamber in fluid communication with the semi-permeable membrane; making a hole at a site from which a liquid sample is desired; evacuating the chamber by applying a vacuum to the chamber; lowering the portable lysimeter into the hole; obtaining a sample in the chamber; and retrieving the lysimeter from the bore; wherein it is not necessary to backfill the bore. A portable lysimeter includes a semi-permeable member and a chamber in fluid communication with the semi-permeable membrane.

17 Claims, 9 Drawing Sheets

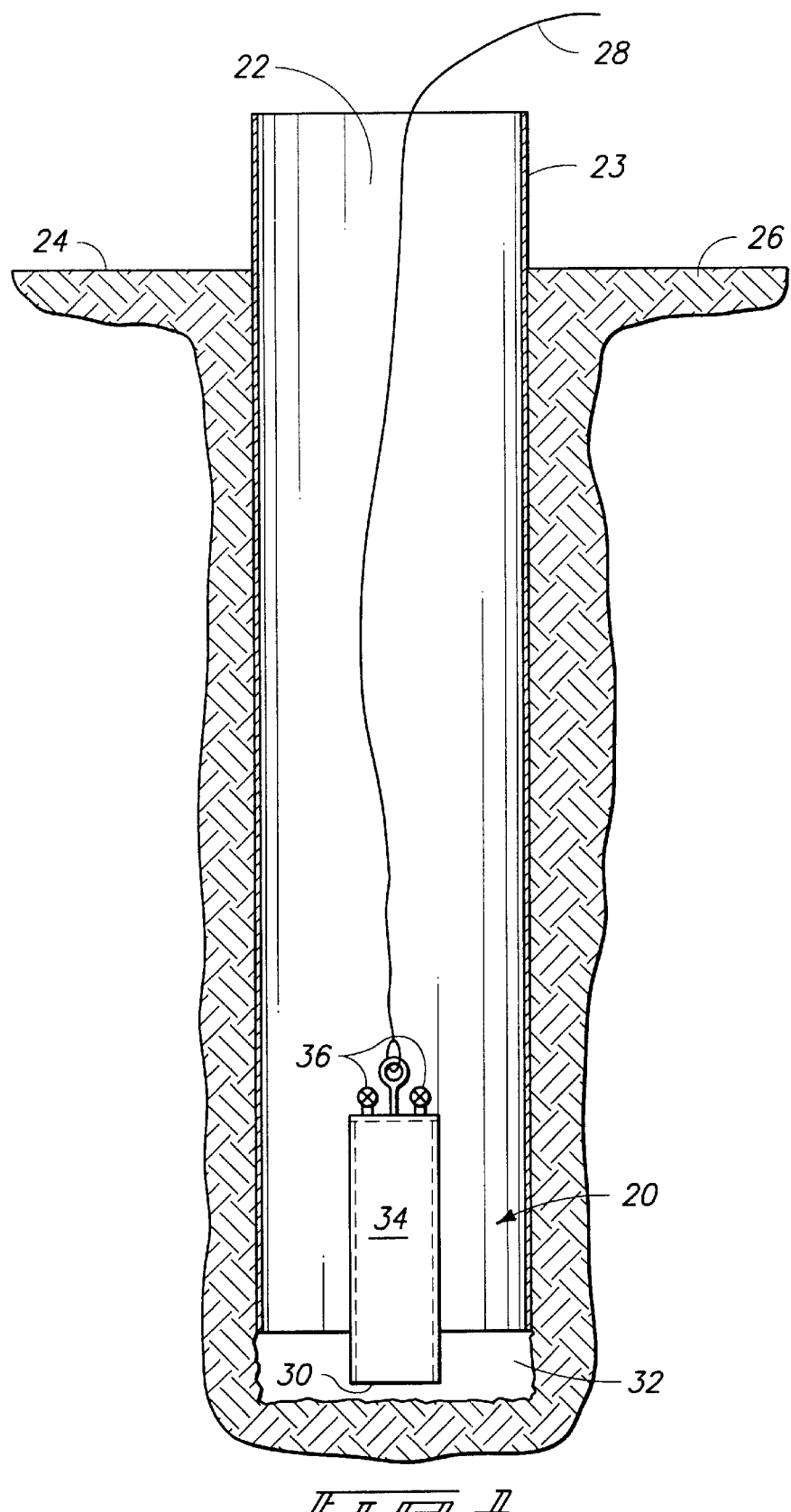

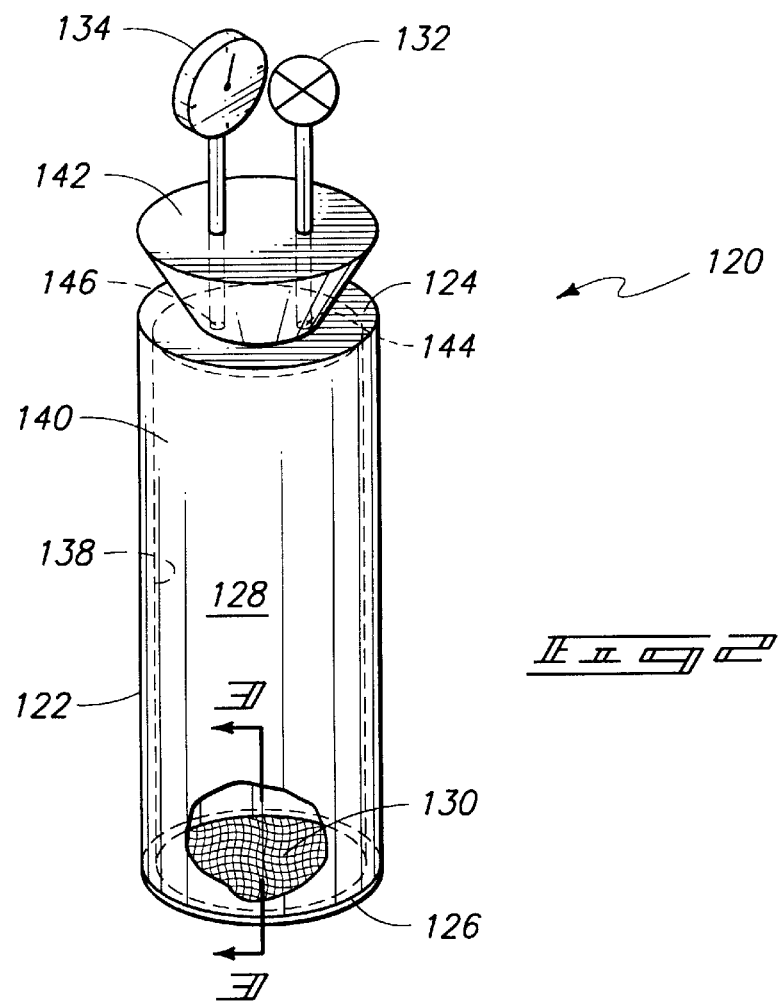
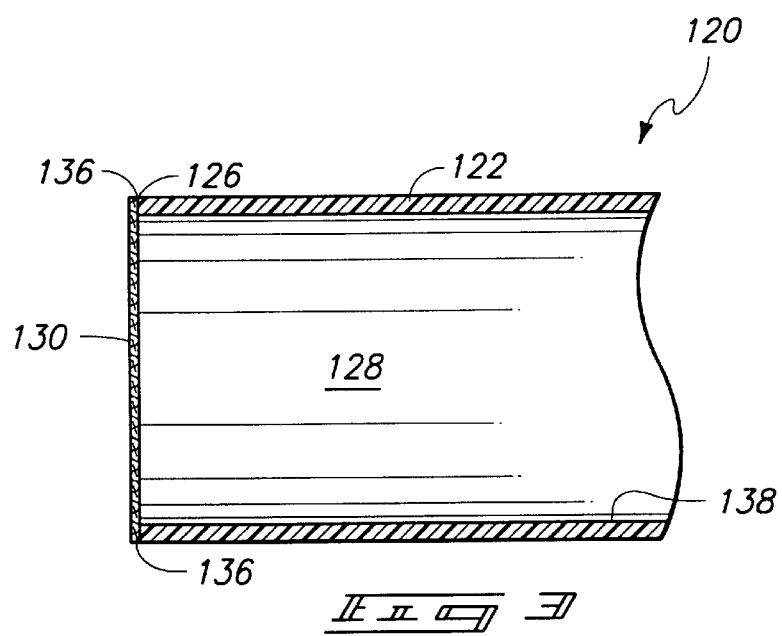

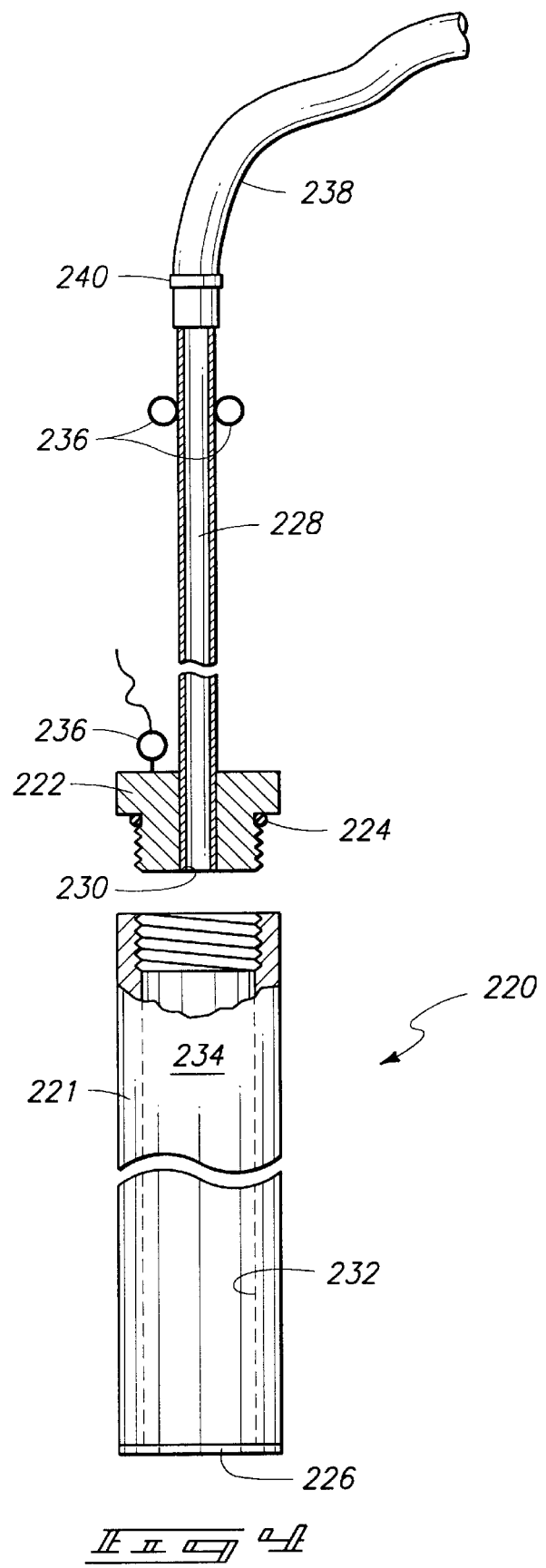

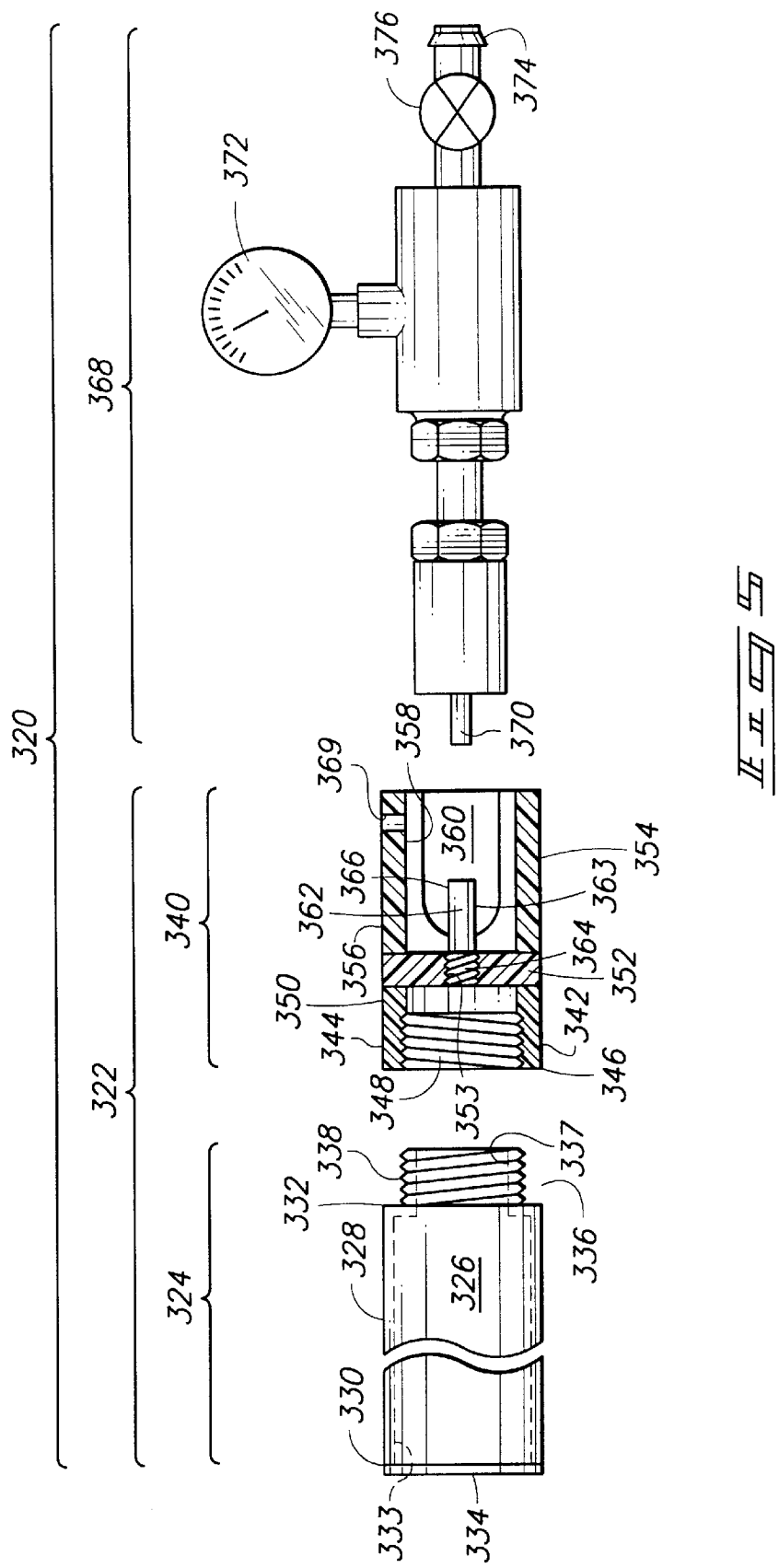

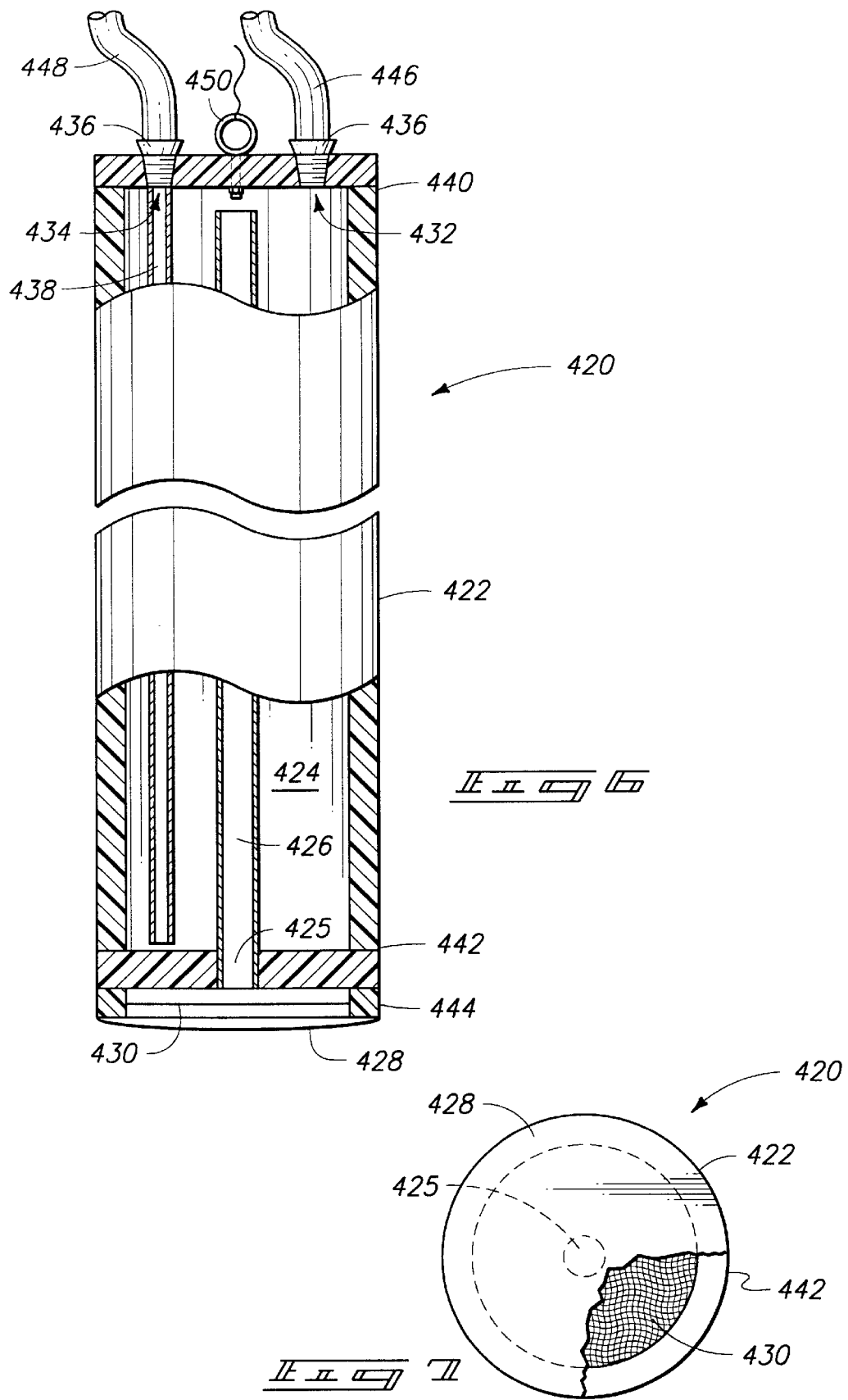

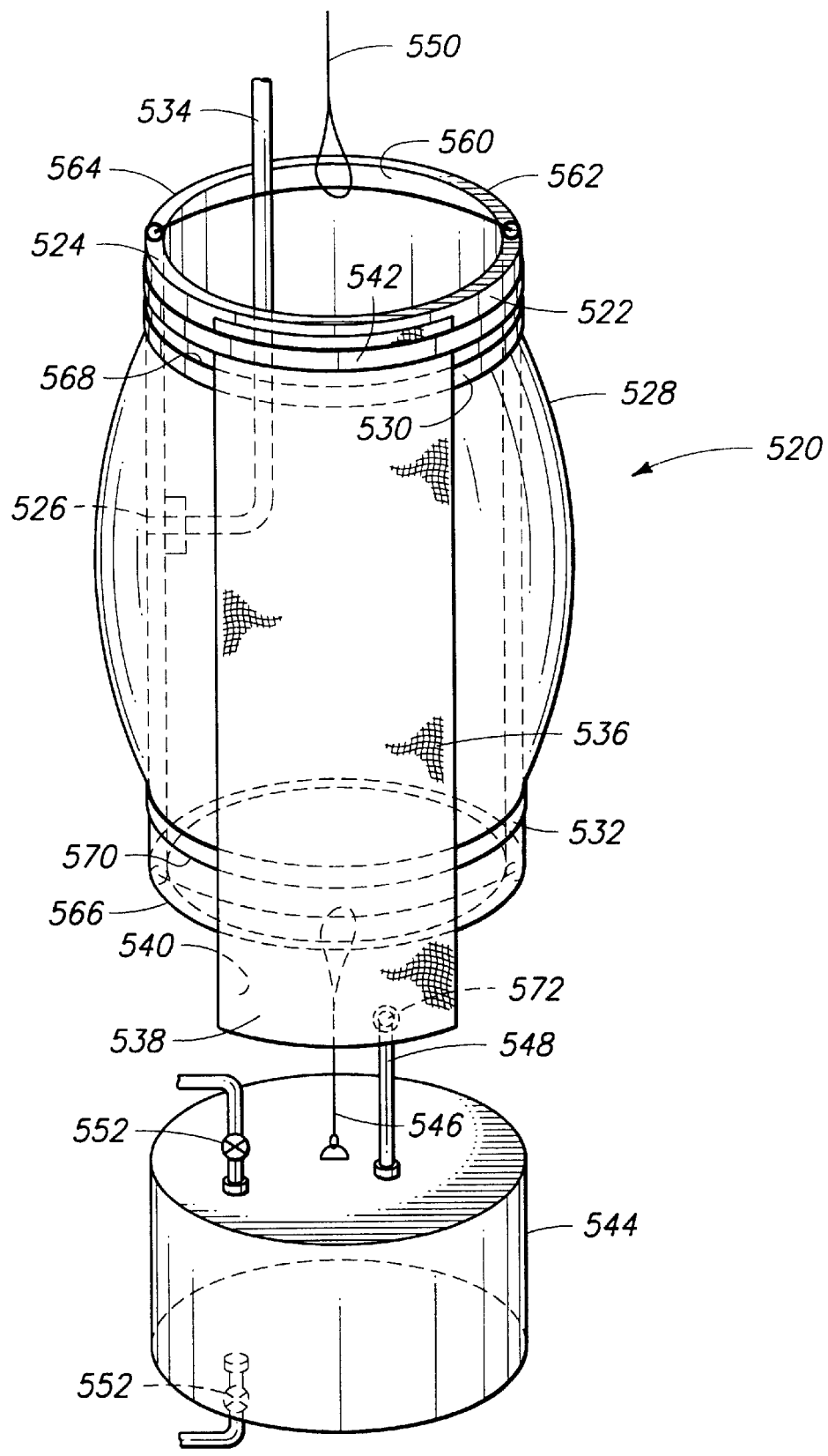

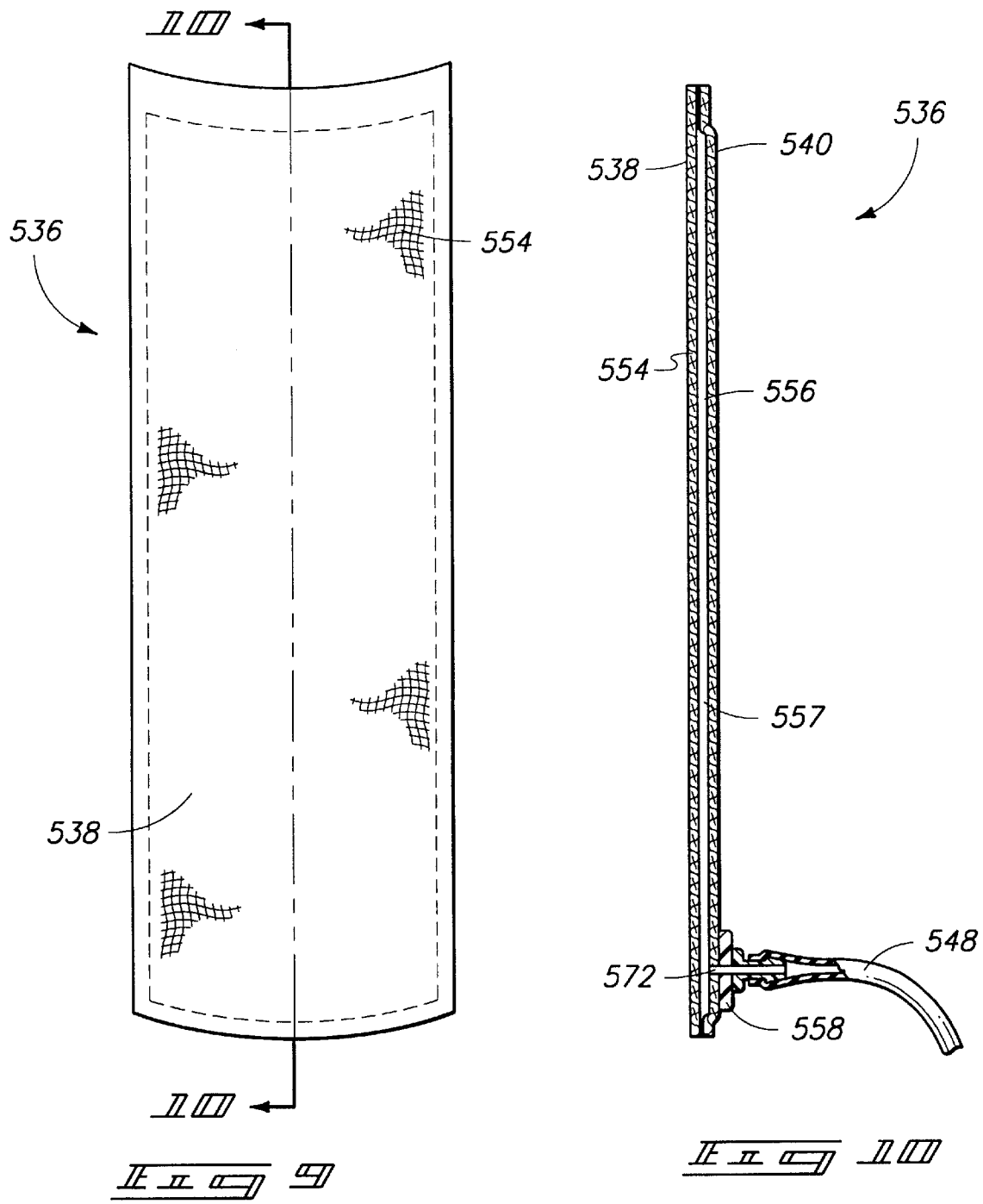

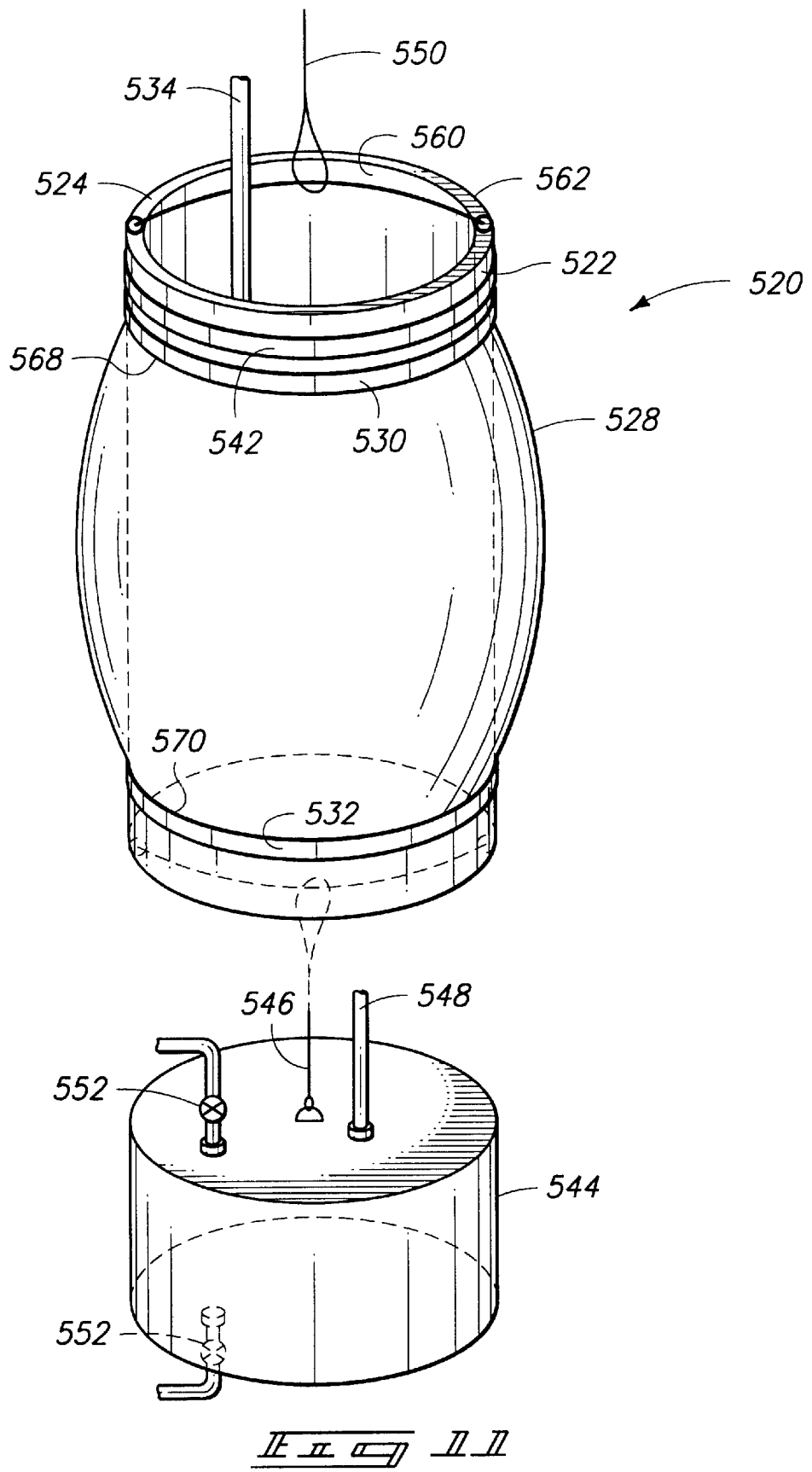

US 6,609,434 B2

METHOD OF RETRIEVING A LIQUID SAMPLE, A SUCTION LYSIMETER, A PORTABLE SUCTION LYSIMETER, A LYSIMETER SYSTEM, AND A DEEP LYSIMETER

CONTRACTUAL ORIGIN OF THE INVENTION

The United States Government has rights in this invention disclosed under contract number DE-AC07-991D1 3233 between the U.S. Department of Energy and Bechtel BWXT Idaho, LLC.

TECHNICAL FIELD

The invention relates to suction samplers and lysimeters. The invention also relates to methods of obtaining liquid samples from wells.

BACKGROUND OF THE INVENTION

As understanding of the effects of soil and water contamination advances, it is increasingly desirable to facilitate groundwater sampling and analysis. Various methods have been employed to extract a soil water sample, including extraction of a soil core, introduction of vacuum-based or absorptive devices or materials, use of suction lysimeters, solution samples, and other methods. There are several types of lysimeters including weighing lysimeters and suction lysimeters. The term "lysimeter," as used below, refers to a suction lysimeter.

A suction lysimeter is a hydrological instrument used to sample liquids or monitor in soil or like substrates. The lysimeter accomplishes this function by application of vacuum or pressure gradient principles such that the liquid of interest is drawn toward the lysimeter permitting collection of a liquid sample. A filter arrangement is frequently employed in conjunction with a lysimeter such that undesired particulate or other solids are not accumulated with the desired sample liquid.

A lysimeter is primarily a sampling device but can also be used to provide an indication of the water pressure (positive or negative). This is done by applying a vacuum, allowing the sampler to pressure equilibrate with the surrounding material being sampled, and then retrieving the sampler to land surface and quickly connecting to a pressure measurement device to obtain an estimate of the in situ soil water potential.

The desired sample liquid is sometimes present only in very thin layers or the material to be sampled may be unsaturated (pores are not filled to capacity with water) and it may be desired to extract liquid samples at various depths within the region of interest; this introduces the difficulty of collecting larger volume liquid samples from the borehole walls of uncased wells at intermediate depths. Another difficulty that is encountered is that the desired liquid may not be flowing freely within the soil but may be held in place by capillary forces. This condition requires the use of vacuum or hydraulic gradient forces to overcome the capillary action and secure the desired sample from its present location, be the sample region saturated or unsaturated.

Liquid sampling with a non-permanent device is performed using several techniques. An absorbent technique (sponge or filter paper) can be used, however this provides small volume samples that are often mixed (contaminated) with sediment/foreign debris.

Prior art devices utilize direct burial or insertion of lysimeter devices into direct contact with the soil region of interest. For example, U.S. Pat. No. 4,759,227 to Timmons teaches of a direct burial method at the sampling location, utilizing a backfill arrangement of bentonite and silica slurry located below, around and above the installed lysimeter. Additional detail is given by Timmons as to the preparation of filter material from a fluoroplastic resin.

In U.S. Pat. No. 4,923,333 to Timmons, the inventor reveals a leak detection scheme utilizing lysimetery at landfills and similar locations. In this case, complete contact burial of the lysimeter(s) is again disclosed.

U.S. Pat. No. 5,000,051 to Bredimeier discloses a lysimeter probe introduced into the ground via force placed upon a horizontal rod or shaft. The instrument is pressed into intimate hydraulic contact with the sediment to be sampled.

U.S. Pat. No. 5,465,628 to Timmons discloses sampling at multiple depths through the installation of a tube body into which a second mechanism may be inserted for extraction of liquids at a level coinciding with any one of several permeable zones located along the length of the installed tube.

BRIEF DESCRIPTION OF THE DRAWINGS

Preferred embodiments of the invention are described below with reference to the accompanying drawings, which are briefly described below.

FIG. 1 is a front elevational schematic showing a suction bailer in accordance with one embodiment of the invention in use in a well.

FIG. 2 is a perspective view of a suction bailer in accordance with an alternative embodiment of the invention.

FIG. 3 is a sectional view taken along line 3—3 of FIG. 2.

FIG. 4 is a perspective view, partly in section, of a suction bailer in accordance with an alternative embodiment of the invention.

FIG. 5 is an exploded view of a suction bailer and detachably coupled evacuation apparatus in accordance with another alternative embodiment.

FIG. 6 is a elevational view, partly in section, of a deep lysimeter in accordance with another embodiment of the invention.

FIG. 7 is a bottom view of the deep lysimeter of FIG. 6.

FIG. 8 is a front elevational view of a suction lysimeter for an uncased well in accordance with another embodiment of the invention, including semi-permeable member assemblies and a water reservoir.

FIG. 9 is a rear view of a semi-permeable member assembly included in the lysimeter of FIG. 8.

FIG. 10 is a side view of the semi-permeable member assembly of FIG. 9.

FIG. 11 is a front elevational view of the suction lysimeter of FIG. 8 with semi-permeable member assemblies removed.

SUMMARY OF THE INVENTION

Figure 12:
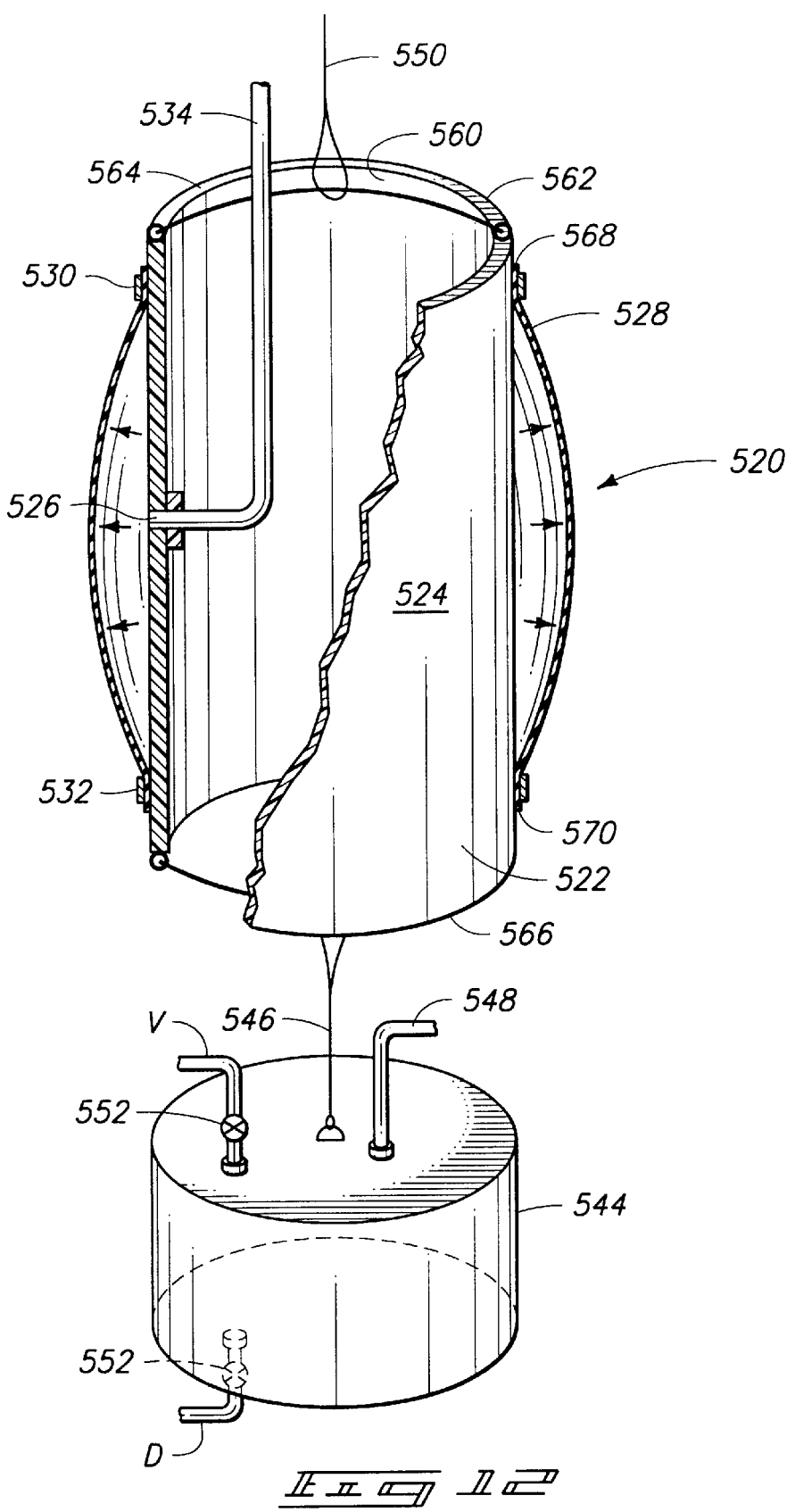
FIG. 12 is a cut away view of the suction lysimeter of FIG. 8 showing inflation of the bladder.

The invention provides a method of retrieving a liquid sample comprising providing a portable lysimeter including a semi-permeable member and a chamber in fluid communication with the semi-permeable member; providing a hole into the earth at a site from which a liquid sample is desired; applying a vacuum pressure to the chamber; lowering the portable lysimeter into the bore; obtaining a liquid sample in the chamber; and retrieving the lysimeter from the bore; wherein it is not necessary to backfill the hole.

Another aspect of the invention provides a portable lysimeter, comprising a tube having an inner surface and an outer surface, a first end, and a second end, and defining a chamber; a semi-permeable member bonded to the first end of the tube; a plug sealing the second end of the tube, the plug having an aperture through it in fluid communication with the chamber; a vacuum line in fluid communication with the aperture and in fluid communication with the chamber via the aperture; a valve in the vacuum line; and line connection structure attached to the lysimeter wherein the lysimeter may be retrieved from the sampling location.

Another aspect of the invention provides a portable lysimeter comprising collection vessel including a cavity defining a collection chamber, a first end including a porous member, and a second, threaded, end; and a connector portion including a first threaded coupling selectively threaded to the second, threaded, end and having a second coupling including a check valve connector including an integral check valve, the check valve connector having a quick-disconnect connector portion for use with a quick-disconnect connector coupled to a pump.

Another aspect of the invention provides a lysimeter system, comprising a portable lysimeter and a selectably attachable pressure measurement device, the portable lysimeter including a collection vessel including a tubular portion having an inner surface and an outer surface having a diameter, the tubular portion having first and second ends, the collection vessel further including a porous member at the first end of the tubular portion, a chamber being defined by the inner surface and the porous member, the collection vessel including a fitting portion extending from the second end of the tubular portion, having an outer threaded cylindrical surface having a diameter less than the diameter of the tubular portion, and having an aperture therethrough in fluid communication with the chamber; a connector portion including a first coupling including a first cylindrical portion having a first end having an inner threaded surface selectively threadable onto outer threaded surface of the fitting portion of the collection vessel and having a second end, the first coupling having an aperture extending from the first end to the second end, the connector portion further including a plate secured to the second end of the first coupling, the plate having a threaded aperture therethrough in fluid communication with the first end of the first coupling, the connector portion further including a second coupling secured to the side of the plate opposite of the first coupling and including a second cylindrical portion and having an inner cylindrical surface, the inner cylindrical surface having an inner diameter and defining a receptacle, the second coupling further including a check valve connector including an integral check valve, the check valve connector having an outer cylindrical surface having a diameter less than the diameter of the inner cylindrical surface, the check valve connector having a threaded portion threadably mounted in the threaded aperture of the plate and having a quick-disconnect connector portion extending from the plate into the receptacle. The pressure measurement device includes a quick-disconnect connector portion being in fluid communication with the pressure measurement device and further being selectably matable with the quick-disconnect connector portion in the receptacle of the connector portion, and including a vacuum gauge in fluid communication with the pressure measurement device, the pressure measurement device further including a barbed fitting in fluid communication with the pressure measurement device, for selective coupling with a pump, wherein fluid communication between the pump and the chamber may be selectably established via the connector portion and pressure measurement device.

Another aspect of the invention provides a lysimeter, comprising a hollow vessel having first and second closed ends and defining a chamber, the first and second ends having respective apertures therethrough; a fill conduit having first and second ends and extending into the chamber from the aperture through the second end of the hollow vessel such that the second end of the fill conduit is between the first and second ends of the vessel; and a semi-permeable member mounted to the second end of the vessel and in fluid communication with the first end of the fill conduit.

Another aspect of the invention provides a deep lysimeter, comprising a body including an inner surface having a diameter, a first end, and a second end, and defining a chamber; a plate having a first surface, and a second surface secured to the second end of the body and having an aperture therethrough; a fill tube including an outer surface having a diameter, a first end, and a second end, the diameter of the outer surface being less than the diameter of the inner surface of the body, the first end of the fill tube being in fluid communication with the chamber via the plate aperture, the fill tube extending into the chamber such that the second end of the fill tube is between the plate and the first end of the body; a spacer having a first surface, and a second surface secured to the first surface of the plate, the spacer having an aperture therethrough; a semi-permeable member mounted to the first surface of the spacer, wherein a cavity is formed bounded by the semi-permeable member, spacer, and plate; a screen supported within the cavity to filter fluid entering the chamber; a cap sealing the first end of the body, the cap having an aperture or apertures in fluid communication with the chamber; and a line connection structure secured to the cap whereby the lysimeter may be retrieved from the sampling location. Valves or plugs are received in the apertures.

Lysimeters of various embodiments of the invention can be installed on a semi-permanent basis in boreholes that either need to be withdrawn for each sampling event or that can be left in place and the sample retrieved without disturbing the sampler. For lysimeters used at shallow depths, e.g., much less than 20 feet, the interior may be designed to allow a vacuum to be provided at land surface to pull samples to the surface, for a nearly permanent installation. For use at greater depths, a lysimeter can be retracted to land surface and the sample withdrawn, or the lysimeter with dual tubes extending to land surface is left at sampling depth and a second tube is pressurized to push the sample to land surface using a first tube. For very deep installations the water reservoir may be separated to two chambers with a one way check valve to prevent the pressure from pushing fluid back through the semipermeable membrane.

For a deep version lysimeter, a vacuum is applied before installation or once installed using a tube that leads to land surface and can attach to an optional vacuum tank. Over time, as a sample moves into the device, the vacuum decreases so there is less driving force to collect additional sample material. The volume of the sample collected can be increased by, for example, enlarging the volume of the vacuum chamber connected to the deep version so that as sample material enters the deep version, it has less of an effect on the change in pressure in the vacuum tank. Alternatively, a vacuum can be reapplied (manually or using an automatic vacuum pump) to keep the pressure relatively constant over time.

Another aspect of the invention provides a portable lysimeter, comprising a body structure; an inflatable bladder supported by the body; a gas conduit in fluid communication with the bladder; a semi-permeable member assembly at least partially movable in response to inflation of the bladder; a sample conduit in fluid communication with the semi-permeable member assembly; and a reservoir supported by the body, and being in fluid communication with the sample conduit.

Another aspect of the invention provides a portable lysimeter, comprising a tube having an outer surface and an inner surface, a first end, and a second end and defining a body, with an aperture therethrough; an inflatable bladder having first and second ends, and an inner tubular surface slidingly telescopically received over the outside surface of the body, the aperture being between the first and second ends of the bladder, such that the bladder covers the aperture, and the bladder being inflatable via the aperture; a first band fitted over the first end of the bladder to secure the first end of the bladder to the body and form a gas-tight seal between the first end of the bladder and the body; a second band fitted over the second end of the bladder to secure the second end of the bladder to the body and form a gas-tight seal between the second end of the bladder and the body; a gas line in fluid communication with the aperture, through which gas may by selectably introduced to inflate the bladder; a plurality of semi-permeable member assemblies, each having a front side, and a back side, located about the outside of the body and having the front side facing away from the body; a belt to secure the semi-permeable member assemblies to the body; a reservoir to collect the sample fluid; a line suspending the reservoir from the body; a sample line fluidly coupling each of the semi-permeable member assemblies and the reservoir, whereby fluid communication is established between each semi-permeable member assembly and the reservoir; and a retrieval line selectably secured to the body using which the lysimeter may be retrieved from the sampling location. If there is a tube leading to the land surface, it can be used to place and remove the lysimeter as desired.

Another aspect of the invention provides a liquid sampling process for collecting a sample of a desired liquid found in an earth cavity, in which the earth cavity has known cross-sectional wall dimensions, comprising the steps of: providing a portable lysimeter having a probe with cross-sectional dimensions sufficiently less than the known cross-sectional dimensions of the earth cavity to enable the portable lysimeter to be lowered and raised in the earth cavity without hindrance; providing the probe with a bottom opening; providing the portable lysimeter with a semi-pervious membrane enclosing the bottom opening of the probe having a solid filter in which the solid filter is air impervious when wetted with a selected liquid, but is pervious to the desired liquid when the desired liquid engages the solid filter; attaching the portable lysimeter to a lowering/lifting line; lowering the portable lysimeter to a desired elevation within the earth cavity while supporting the lysimeter in the earth cavity by the lowering/lifting line for enabling the desired liquid to engage the solid filter; applying a vacuum pressure of a sufficient magnitude for causing a sample of the desired liquid to pass through the wetted solid filter and into the probe when the desired liquid engages the solid filter; and after the sample of the desired liquid passes into the probe, raising the portable lysimeter with the lowering/raising line from the earth cavity.

Still another aspect of the invention provides a liquid sampling apparatus for collecting a sample of a liquid found in an earth cavity, in which the earth cavity has known cross-sectional dimensions, comprising: providing a portable lysimeter probe having cross-sectional dimensions less than the known cross-sectional dimensions of the earth cavity; said lysimeter probe having an open substantially planar bottom wall; a substantially planar semi-permeable member affixed to the probe enclosing the bottom wall to provide an air impervious enclosure when the member is wetted with a selected liquid and provide a liquid pervious enclosure to enable the desired liquid to pass through the member into the interior probe when the desired liquid engages the solid filter; a lowering/raising line attached to the probe for lowering the probe into the earth cavity and supporting the probe at a desired level to enable the desired liquid to engage the member and for raising the probe from the earth cavity after a sample of the desired liquid has been collected; and a vacuum generator attachable to the probe for creating a vacuum of sufficient magnitude within the probe to draw a sample of the desired liquid through the filter and into the probe when the desired liquid engages the solid filter.

Another aspect of the invention provides a suction bailer or lysimeter which can collect liquid samples of variable volumes and containerizes a sample in a relatively clean environment until the liquid is removed. This idea of a portable lysimeter was not considered feasible because it was previously thought that there had to be firm contact with the material being sampled and the sampling device; the inventors have determined that this is not the case.

DETAILED DESCRIPTION OF THE PREFERRED EMBODIMENTS

FIG. 1 shows a portable fluid sampling device or lysimeter 20 for collection of fluid samples in either the saturated or unsaturated zone. It can be used, for example, for collecting water samples from the vadose zone, ground water, geologic media, or buried waste.

The suction bailer or lysimeter 20, in accordance with one embodiment of the invention, can collect water in very thin layers of standing water (e.g., <1 mm deep) or unsaturated porous material (need to make a partial hydraulic connection to material if unsaturated). It can also collect fluid from discrete depths. The device 20 can be used to selectively collect water or other fluids from a mixture of a fluid mixed with a solid. In one embodiment, the device can remove fluids where the fluid is held by capillary forces at pressures from above saturation to a theoretical limit of about −1.0 atmosphere, though a practical limit has been observed at about −0.5 atmosphere (−7.3 psi) relative to atmospheric pressure.

The device 20 can be used, for example, to collect fluid samples from intermittent sources of water (i.e. waiting for a fluid to come in contact with the device and then collect and hold a fluid sample until an operator removes the sample). In one embodiment, the samples that are removed from the device 20 are filtered to remove particulate matter (various filter sizes can be used). The combination of portability along with other sampling characteristics makes the device 20 useful for environmental/industrial applications.

FIG. 1 shows the lysimeter 20 in its simplest form. It is a portable sampling device used to collect fluid (water or other fluid) located in the saturated or unsaturated zone within a hole 22 excavated through existing materials 26 (having a well casing 23 shown in FIG. 1) at the location of interest and extending to the desired depth below the surface 24. In a typical sampling situation, the saturated zone is that depth or strata of the hole in which the surrounding media (earth or other material) is completely imbued with liquid, to the exclusion of additional liquid entering the same region. The unsaturated zone has liquid present within the surrounding media, but not in sufficient quantity as to prevent additional liquid from entering the same region. The lysimeter 20 includes a chamber 34 and semi-permeable or porous member 30 in fluid communication with the chamber 34. The lysimeter 20 is lowered into the hole 22 via a line 28 until contact is made between the semi-permeable member 30 of the lysimeter 20 and fluid bearing strata 32. In operation, a vacuum pressure applied to the chamber 34 to draw the fluid sample into the chamber 34 through the semi-permeable member 30 and maintain the sample until the lysimeter 20 is retrieved via the line 28. In operation, the semi-permeable member 30 is typically wet up with fluid (known as wetting fluid) so that a vacuum-pressurized condition of the chamber 34 is maintained until contact is established between the semi-permeable member and the target fluid. The lysimeter 20 includes valves 36 in fluid communication with the chamber 34 for connection to a pump and/or for draining of the fluid sample at retrieval time. The lysimeter may also have a conduit to the surface 24 so that continuous vacuum pressure may be applied without requiring that the vacuum pump be lowered into the hole. This yields an extremely simple technique for securing and retrieving the fluid sample.

FIG. 2 shows a portable lysimeter 120 in accordance with an alternative embodiment of the invention. The lysimeter 120 includes a tube 122 having an inner surface 138 and an outer surface 140. The tube 122 is formed of plastic, such as clear or translucent plastic, in one embodiment, or metal or other suitable rigid material. The tube 122 further has a top 124, and a bottom 126. The lysimeter further includes a resilient stopper 142 or other suitable seal selectively closing the top 124 of the tube 122, and a semi-permeable member 130. Semi-permeable member 130 is supported by or secured to the bottom 126 of the tube 122. In an alternative embodiment, the top 124 is closed or integral with the inner surface 138 and the stopper 142 is omitted. Other suitable methods of sealing top 124 may be employed. The inner surface 138, top 124, bottom 126, stopper 142 and semi-permeable member 130 collectively define a chamber 128. The lysimeter 120 further includes a valve 132 in fluid communication with the chamber 128 via an aperture 144 through the stopper 142. The valve 132 may be used to connect a pump to pre-evacuate the chamber 128, to connect a continuously applied vacuum pressure, or to drain the collected sample. The lysimeter 120 further includes a vacuum gauge 134 in fluid communication with the chamber 128 via an aperture 146 through the stopper 142, and may be used to monitor the degree of chamber 128 pressurization.

FIG. 3 shows that the semi-permeable member 130 is secured to the tube bottom 126 via glue 136, in one embodiment. Other methods could, of course, be employed.

FIG. 4 shows a portable lysimeter 220 in accordance with an alternative embodiment of the invention. The lysimeter 220 comprises a tube 221, having an inner surface 232, and further having a top 222 that is selectably detachable from the tube 221 for removal of the sample. The top 222 has a through aperture 230, and the lysimeter 220 further includes a vacuum tube 228 in fluid communication with the aperture 230 or extending from partially or completely through the aperture. The lysimeter 220 further includes a vacuum line 238 and a clamp 240. The vacuum line 238 is in fluid communication with vacuum tube 228 and secured to the vacuum tube 228 with the clamp 240, such that a vacuum pressure may be applied to the chamber 234 via the vacuum line 238 leading to the land surface. The lysimeter 220 further includes an O-ring 224 that enhances the seal between the top 222 and the tube 221 during the mating of these components. The lysimeter 220 further includes semi-permeable member 226 that is supported by or secured to the bottom end of the tube 221. The top 222, inner surface 232, semi-permeable member 226 collectively define a chamber 234. The lysimeter 220 further includes retrieval loops or apertures 236 which selectively receive a line for raising, lowering, or supporting the lysimeter 220 and line 238.

FIG. 5 shows a lysimeter system 320 in accordance with another embodiment of the invention. The lysimeter system 320 comprises a portable lysimeter 322. The portable lysimeter 322 includes a collection vessel 324. The collection vessel 324 includes a tubular portion 328, having an inner surface 333, an end 330, and an end 332. The collection vessel 324 further includes a semi-permeable member 334 supported by or secured to end 330 of the tubular portion 328. The collection vessel 324 further includes a chamber 326 defined by the inner surface 333 of the tubular portion 328 and semi-permeable member 334. In the illustrated embodiment, the semi-permeable member 334 is in the form of a plate. In alternative embodiments, the semi-permeable member 334 (or 226, or 130, etc.) can be a porous cup, and can be made of ceramic, plastic, glass, or metal, and may be rigid or may be partially or wholly flexible. Other forms such as a cluster of fibers (not shown), capable of wicking a sample liquid into the chamber, may also be used. The semi-permeable member 334 can be formed integrally with the end 330 of the tubular portion 328 or secured to the end 330 in any appropriate manner, such as by bonding with glue, securing with screws, securing the screen embodiment with a hose clamp or similar sealing mechanism to the outer wall of the tubular portion 328, etc.

The collection vessel 324 includes a fitting portion 336 extending from the end 332 of the tubular portion 328. In the illustrated embodiment, the fitting portion 336 has an outer threaded cylindrical surface 338 having a diameter less than the diameter of the tubular portion 328, and has a through aperture 337 in fluid communication with the chamber 326.

The portable lysimeter 322 further includes a connector portion 340 including a coupling 342. The coupling 342 includes a cylindrical portion 344 having an end 346. In alternative embodiments, other shapes are employed. The end 346 has an inner threaded surface 348 selectively threadable onto the outer threaded surface 338 of the fitting portion 336 of the collection vessel 324. The first coupling 342 further has a second end 350. In alternative embodiments (not shown), the fitting portion of the collection vessel can have an inner threaded surface and the first end of the first cylindrical portion can have an outer threaded surface. The first coupling 342 further has an aperture extending from the end 346 to the end 350.

The connector portion 340 further includes a barrier or plate 352 secured to the end 350 of the coupling 342. The barrier or plate 352 has a threaded aperture 353 in fluid communication with the end 346 of the coupling 342. The connector portion 340 further includes a coupling 354 extending from, supported by, or secured to the side of the plate 352 opposite of the coupling 342 or integral with the cylindrical portion 344. The coupling 354 includes a cylindrical portion 356 and having an inner cylindrical surface 358. In alternative embodiments, other shapes are employed. The inner cylindrical surface 358 has an inner diameter and defines a receptacle 360.

The coupling 354 further includes a check valve connector 362 having an integral check valve. Suitable connectors are available from Swageloc of Solon, Ohio. The check valve connector 362 includes an outer cylindrical surface 363 having a diameter less than the diameter of the inner cylindrical surface 358. The check valve connector 362 has a threaded portion 364 threadably mounted into the threaded aperture 353 of the plate 352. In alternative embodiments, the check valve connector is non-threadably supported by the plate 352. The check valve connector 362 further has a quick-disconnect connector portion 366 extending from the plate 352 into the receptacle 360. The coupling 354 further includes one or more through apertures 369 such that selectable connection of a line (not shown) may be used to retrieved the lysimeter 322 from a sampling location. Alternatively, a loop or eyebolt is provided anywhere appropriate on the lysimeter 322 for receipt of a removal line.

The overall arrangement of the connector portion 340 is readily constructed from available components and facilitates easy interface of the collection vessel 324 to an evacuation arrangement to be described hereafter. Additionally, the connector portion 340 may be easily removed from the collection vessel 324 to allow draining of the collected fluid sample.

The lysismeter system 320 further includes a pressure measurement device 368. The pressure measurement device includes a quick-disconnect connector portion 370 selectably matable with the quick-disconnect connector portion 366 in the receptacle 360. The pressure measurement device 368 further includes a vacuum gauge 372, a valve 376, and a barbed fitting 374, such that the three are in common fluid communication with the quick-disconnect connector portion 370. The barbed fitting 374 permits selective coupling of a pump (not shown) to the collection vessel 324 via the pressure measurement device 368 and connector portion 340. Due to the compact size and portable nature of the lysimeter system 320, a hand actuated pump may be utilized, realizing a portable lysimeter 322 that can be vacuum pressurized and placed into service in remote areas without need for power.

FIG. 6 shows a lysimeter 420 in accordance with another embodiment of the invention. This embodiment may be retrieved from the sampling location to gather the liquid sample, or left in place while the sample is extracted by pressure or vacuum means and transported to the land surface. The lysimeter 420 includes a tube 422 having closed ends 440 and 442. The tube 422 defines a chamber 424. The lysimeter 420 further includes an aperture 425 through the end 442, and further includes apertures 432 and 434 through the end 440. The lysimeter 420 further includes a fill tube 426 in fluid communication with the aperture 425 and extending into the chamber 424. The lysimeter further includes a spacer 444, a screen 430 as required, and a semi-permeable member 428. The screen 430 is optional if the semi-permeable member is rigid. The spacer 444 is secured to the end 442 of the tube 422. The semi-permeable member 428 is secured to the spacer 444 opposite of the end 442. The configuration of closed end 442, spacer 444, and semi-permeable member 428 form a cavity, and further support screen 430 (if a flexible membrane) within the cavity. Semi-permeable member 428 and screen 430 are in fluid communication with the chamber 424 via the aperture 425 and fill tube 426. The lysimeter optionally further includes valves, plugs, or fittings 436 respectively received in each of the apertures 432 and 434 in fluid communication with the chamber 424. In one alternative embodiment, one plug is provided in one of the apertures 432 and 434 and one valve is provided in one of the apertures 432 and 434.

The lysimeter 420 further includes a sample extraction tube 438 in fluid communication with the aperture 434 and respective fitting 436, and extending into the chamber 424 toward the end 442 of the tube 422. The lysimeter 420 may be selectably connected to a pump for vacuum pressurization of the chamber 424 via the fitting 436 in the aperture 432. The fitting 436 in the aperture 434 may be utilized to drain the collected sample fluid from the chamber 424. Selectably stopping the first aperture 432 and the second aperture 434 by blocking the respective fittings 436 maintains the vacuum pressure while the lysimeter is being placed into service. Other uses for the fittings 436 may also be realized. For example, optional tubes 446 and 448 in fluid communication with respective fittings 436 may be used to deliver the fluid sample to the land surface, by pressurizing the chamber 424 through optional tube 446 such that the fluid sample is transported to the land surface through optional tube 448.

The fill tube 426 and chamber 424 arrangement retains the sample fluid until the lysimeter is retrieved by an operator, and further serves to reduce the loss of fluid from backflow of fluid contained in chamber 424. Further, a one way flow valve or check valve (not shown), may be used instead of the fill tube 426 to protect the semi-permeable member 428 and/or screen 430 from excessive pressure when the sample is being retracted from the hole by applying pressure into chamber 424 by way of tube 446. Lysimeter 420 further includes a line connection structure 450 secured to the closed end 440. Selective attachment of a line to structure 450 facilitates raising, lowering, or supporting the lysimeter 420.

FIG. 7 shows an end view of the portable lysimeter 420 of FIG. 6, including a typical arrangement of the semi-permeable member 428, the screen 430, the aperture 425 and the end 442 of the tube 422.

FIG. 8 shows a portable lysimeter 520, in accordance with an alternative embodiment of the invention. The lysimeter 520 includes a tube 522 having an inner surface 560 and an outer surface 562, an end 564, and an end 566. The tube 522 defines a body 524, having an aperture 526. The lysimeter 520 further includes an inflatable bladder 528, having ends 568 and 570 and an inner tubular surface slidingly telescopically received over the outside surface of the body 524. The aperture 526 is located between the ends 568 and 570 of the bladder 528, such that the bladder 528 covers the aperture 526. The bladder 528 is inflatable via the aperture 526. The lysimeter 520 further includes a band 530 fitted over the end 568 of the bladder 528 to secure the end 568 of the bladder 528 to the body 524 and form a gas-tight seal between the end 568 of the bladder 528 and the body 524. The lysimeter further includes a band 532 fitted over the end 570 of the bladder 528 to secure the end 570 of the bladder 528 to the body 524 and form a gas-tight seal between the end 570 of the bladder 528 and the body 524.

The lysimeter 520 further includes a gas line 534 in fluid communication with the aperture 526, through which gas may by selectably introduced to inflate the bladder 528. The lysimeter 520 further includes a plurality of semi-permeable member assemblies 536. Each assembly 536 has a front side 538, and a back side 540, located about the outside of the bladder 528. The front side 538 of each assembly 536 faces away from the body 524. The lysimeter 520 further includes a belt 542 securing the semi-permeable member assemblies 536 to the body 524 at respective locations beyond the end of the bladder 528 such that the belt 542 does not hinder the inflation of the bladder 528. The lysimeter further includes a reservoir 544 to collect the sample fluid. While reservoir 544 is shown as being separate from tube 522, in one embodiment a single part defines both reservoir 544 and tube 522. The lysimeter further includes a line 546 and associated structure such that the body 524 supports the reservoir 544 via the line 546.

The lysimeter 520 further includes a sample line 548 fluidly coupling each of the semi-permeable member assemblies 536 and the reservoir 544. The sampler line 548 provides a conduit through which sample fluid collected by the respective semi-permeable member assemblies 536 is transported to the reservoir 544. The lysimeter 520 further includes a plurality of valves 552 each respectively in fluid communication with the reservoir 544. The reservoir 544 has an interior that defines a chamber. The lysimeter 520 further includes a retrieval line 550 that is selectably secured to the body 524 permitting retrieval of the lysimeter 520 from the sampling location. More particularly, the lysimeter 520 includes a diametrically extending wire or line attached to the end 564 of the tube 522 to which the line 550 can be tied.

In operation, the semi-permeable member assemblies 536 are wet up with wetting fluid, and the chamber is vacuum pressurized prior to placement into service. The lysimeter 520 is lowered into a sample hole, with support provided by the retrieval line 550. The bladder 528 is then inflated via the gas line 534 until the bladder 528 has expanded sufficiently to urge at least a portion of the front side 538 of each semi-permeable member assembly 536 into contact with the interior of the hole. Fluid traveling along the walls of the hole and coming into contact with the front side 538 of any semi-permeable member assembly 536 is captured and routed to the reservoir 544 for collection. To gather the fluid sample, the bladder 528 is deflated via the gas line 534 prior to retrieval and the lysimeter 520 is then brought to the surface via the retrieval line 550. The collected fluid sample may then be selectably drained from the chamber. In one embodiment, retrieval of the sample fluid is facilitated by a collection line extending from one of the valves 552 (e.g., the top valve) to the land surface to allow a vacuum to be applied once the lysimeter 520 placed in the hole and the bladder expanded.

FIGS. 9 and 10 show front and side views, respectively, of a typical embodiment of the semi-permeable member assembly 536. The front side 538 comprises flexible semi-permeable material 554. The back side 540 is secured to the front side 538 via cement about the periphery. The semi-permeable member assembly 536 includes scrim material 556 that maintains a cavity 557 between the front side 538 and the back side 540, with the cavity in fluid communication with the flexible semi-permeable material 554. The back side 540 of the semi-permeable member assembly 536 further includes an aperture 572. The semi-permeable member assembly 536 further includes with a plate fitting 558 in fluid communication with the cavity 557 via the aperture 572. The plate fitting 558 provides fluid communication to the reservoir 544 via the sample line 548.

FIG. 11 provides an illustration of the portable lysimeter 520 with the semi-permeable member assemblies 536 not shown, for clarity. The bladder 528 typically underlying the semi-permeable member assemblies 536 (not shown in FIG. 11) is fully exposed.

FIG. 12 provides a cutaway view of the lysimeter 520 such that further details of a typical bladder 528 and gas line 534 arrangement are revealed. Further shown are typical designations for vacuum V and drain D connections to the valves 552 included at the reservoir 544.

Under typical operation the portable lysimeter is left in place in a hole to collect the sample for a time period and then retrieved to the surface to remove the sample for analysis. The semi-permeable member(s) utilized on any given embodiment are commercially available from a variety of suppliers. They may be made of porous metals, ceramics, glass or plastics. The semi-permeable member is generally wetted with deionized water or with water of known quality prior to sampling to fill the pores and prevent air entry into the device. More particularly, in the various embodiments, the semi-permeable member is generally wet up with fluid (known quality of wetting fluid) and a vacuum is applied prior to lowering into the hole. The semi-permeable member generally will not hold a vacuum (air enters the device) unless the semi-permeable member has been pre-wetted. An exception is if there is standing water in the hole, in which case the lysimeter could be lowered so that the semi-permeable member is in contact with the water, and then a vacuum is applied following the lowering. This requires a tube to the lysimeter from the land surface. Also, the semi-permeable member has pores sized to transmit water but exclude air transport across the member.

The lysimeter may include a removable top to allow the chamber to be cleaned and emptied. A disposable version (not shown) just has a way to seal the chamber, apply a vacuum pressure and then remove the sample.

If the semi-permeable member of the lysimeter is supported an appropriate distance above the material or fluid to be sampled, then it will only collect the fluid if the fluid level rises to the level of the semi-permeable member. It may, for example, be used to collect intermittent sources of water such as perched water or when the fluid level reaches a given depth. The lysimeter can also be used to collect water from discrete depths by pressurizing the chamber, lowering it to a specified depth, then applying a vacuum pressure to the chamber to collect a sample. This configuration also allows samples to be collected from very thin layers of fluids and to accumulate large samples. This fluid is also filtered while collecting the sample. Several different pore-sized materials are commonly available that would be acceptable.

The various semi-permeable members 30, 130, 226, 334, and 428 can be flat, slightly rounded, or in cup shape or highly rounded shape. One type of semi-permeable member is called a hollow fiber, is used for dialysis, and looks like a hollow thread. These fibers come in different pore sizes and is used, in one embodiment, in place of the semi-permeable member of the various embodiments. For example, the hollow fibers are cut to three to six inch lengths, both cut ends are placed in the end of a long tube with the loop extending out below and the cut fiber ends in the tube. A sealant is used to pot the fibers in place (with the loops extending out below the tube and the cut ends open to the inside of the tube). The tube is sealed on the top, a partial vacuum is applied to the tube, and the fibers are placed in contact with the material to be sampled. Sample fluid is pulled through the fibers in the tube. The tube is then pulled to the land surface for sample collection.

Thus, a sampling mechanism or lysimeter has been provided that is easily transportable, being of size that is easily handled in the field. This aspect permits servicing of several installed locations within a typical work period.

Further, a portable lysimeter has been provided capable of using a vacuum pressure technique to urge the sample fluid into a collection chamber, with the vacuum pressure existing as either a pre-pressurized state within the collection chamber or via communication between the chamber and a remotely located pump, typically at the surface of the ground. In the pre-pressurized mode, no connection between the in-service lysimeter and any vacuum system is required. This mode permits operation with a reduced equipment count and eliminates the need to install, maintain or energize vacuum pump devices in remote areas.

A method has been provided to extract fluid samples from a well or borehole in such manner that backfill or direct burial is not required. This allows for repeated use of the same sample location, typically part of a matrix of strategically located sampling boreholes, without the need to excavate the installed location at sample gathering time or backfill the borehole when a fresh lysimeter is placed into service. This eliminates considerable labor and heavy machine operating time. Further, a lysimeter suspect of malfunction may be easily retrieved and replaced.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of retrieving a liquid sample, comprising:
    providing a portable lysimeter including a semi-permeable member and a chamber in fluid communication with the semi-permeable member;
    providing a hole at an earth site from which a liquid sample is desired;
    applying a vacuum pressure to the chamber;
    lowering the portable lysimeter into the hole;
    obtaining a liquid sample in the chamber; and
    retrieving the lysimeter from the hole; wherein it is not necessary to backfill the hole.

2. A method of retrieving a liquid sample in accordance with claim 1 wherein the vacuum pressure is applied prior to the lowering.

3. A method of retrieving a liquid sample in accordance with claim 1 and further comprising wetting the semi-permeable membrane prior to the lowering so as to maintain the vacuum pressure of the chamber during the lowering.

4. A method of retrieving a liquid sample in accordance with claim 1 wherein the semi-permeable membrane is located below the chamber.

5. A portable lysimeter, comprising: p1 a tube having a inner surface and an outer surface, a first end, and a second end, and defining a chamber;
    a semi-permeable member first end of the tube;
    a plug sealing the second end of the tube, the plug having an aperture therethrough in fluid communication with the chamber;
    a vacuum line in fluid communication with the aperture and in fluid communication with the chamber via the aperture;
    a valve in the vacuum line; and
    line connection structure attached to the lysimeter wherein the lysimeter may be retrieved from the sampling location.

6. A portable lysimeter in accordance with claim 5 wherein the plug has a second aperture therethrough, the lysimeter further comprising a vacuum gauge in fluid communication with the second aperture.

7. A portable lysimeter in accordance with claim 5 wherein the plug comprises a stopper.

8. A portable lysimeter in accordance with claim 5 wherein the semi permeable member comprises a porous member.

9. A portable lysimeter in accordance with claim 5 wherein the semi-permeable member comprises porous PCV.

10. A portable lysimeter in accordance with claim 5 wherein the semi-permeable member comprises porous metal.

11. A portable lysimeter in accordance with claim 5 wherein the semi-permeable member comprises porous glass.

12. A portable lysimeter in accordance with claim 5 wherein the semi-permeable member comprises porous ceramic.

13. A portable lysimeter in accordance with claim 5 wherein the semi-permeable member comprises porous plastic.

14. A portable lysimeter in accordance with claim 5 wherein the line connection structure comprises an eye bolt.

15. The portable lysimeter of claim 5 wherein the plug comprises a connector portion including a first threaded coupling selectively threaded to the second end of the tube.

16. The portable lysimeter of claim 15 further comprising a coupling including a check valve connector including an integral check valve connected to a second end of the connector portion, the check valve connector having a quick-disconnect connector portion for use with a quick-disconnect connector coupled to a pump.

17. A liquid sampling apparatus for collecting a sample of a liquid found in an earth cavity, in which the earth cavity has known cross-sectional dimensions, comprising:
    a portable lysimeter probe having cross-sectional dimensions less than the known cross-sectional dimensions of the earth cavity;
    the lysimeter probe having an open substantially planar bottom wall;
    a substantially planar semi-permeable member affixed to the probe enclosing the bottom wall to provide an air impervious enclosure when a solid filter is wetted with a selected liquid and provide a liquid pervious enclosure to enable the desired liquid to pass through the member into the interior probe when the desired liquid engages the member;
    a lowering/raising line attached to the probe for lowering the probe into the earth cavity and supporting the probe at a desired level to enable the desired liquid to engage the solid filter and for raising the probe from the earth cavity after a sample of the desired liquid has been collected; and
    a vacuum generator attachable to the probe for creating a vacuum of sufficient magnitude within the probe to draw a sample of the desired liquid through the filter and into the probe when the desired liquid engages the solid filter.

* * * * *